(12) United States Patent
Alpeter et al.

(10) Patent No.: US 8,334,362 B2
(45) Date of Patent: Dec. 18, 2012

(54) METHOD AND APPARATUS FOR DETERMINING MELT ELASTICITY

(75) Inventors: Mark D. Alpeter, Lake Jackson, TX (US); Marc A. Mangnus, Clinge (NL); Charles M. Cheatham, Lake Jackson, TX (US); Marinus G. Nieuwenhuize, Hoek (NL); Jack M. Potter, Jr., Angleton, TX (US)

(73) Assignee: Dow Global Technologies LLC, Midland, MI (US)

( * ) Notice: Subject to any disclaimer, the term of this patent is extended or adjusted under 35 U.S.C. 154(b) by 605 days.

(21) Appl. No.: 12/553,156

(22) Filed: Nov. 18, 2009

(65) Prior Publication Data

US 2011/0103425 A1     May 5, 2011

Related U.S. Application Data (60) Provisional application No. 61/190,850, filed on Sep. 3, 2008.

(51) Int. Cl.
*C08F 6/00* (2006.01)
*C08G 63/00* (2006.01)

(52) U.S. Cl. ............... 528/500; 73/829; 374/49

(58) Field of Classification Search ............ 73/829; 374/49; 528/500
See application file for complete search history.

(56) References Cited

U.S. PATENT DOCUMENTS

| 4,680,958 A | 7/1987 | Ruelle et al. |
| 5,347,851 A | 9/1994 | Grudzien, Jr. et al. |

FOREIGN PATENT DOCUMENTS

| DE | 19505250 C1 | 8/1996 |
| EP | 1174261 A1 | 1/2002 |
| JP | 2004138601 A | 5/2004 |

OTHER PUBLICATIONS

Wagner, M.H., et al: "Rheotens-mastercurves and Drawability of Polymer Melts", Polymer Engineering and Science, vol. 36, No. 7, Apr. 1, 1996, pp. 925-935, Brookfield Center, US.

Wagner, M.H., et al: "The Rheology of the Rheotens Test", J. Rheologica., vol. 42(4), Jul./Aug. 1998, pp. 917-928, The Society of Rheology, Inc., 1998.

*Primary Examiner* — Terressa Boykin

(57) ABSTRACT

An apparatus and method for determining the standardized melt elasticity (sME) force of a thermoplastic polymer needed to stretch a strand of melted polymer at a speed about thirty three times faster than the speed of strand formation from a body of melted polymer under constant stress from an unencumbered dead weighted piston.

15 Claims, 7 Drawing Sheets

METHOD AND APPARATUS FOR DETERMINING MELT ELASTICITY

CROSS REFERENCE TO RELATED APPLICATIONS

This application claims priority from U.S. Provisional Application Ser. No. 61/190,850 filed Sep. 3, 2008. For purposes of United States patent practice, the contents of this application is herein incorporated by reference in its entirety.

BACKGROUND OF THE INVENTION

The instant invention is in the field of methods and apparatus for the measurement of viscoelastic properties of molten thermoplastic polymers. More specifically, the instant invention relates to methods and apparatus for the determination of melt elasticity.

As stated in Wagner and Bernnat, J. Rheol. 42(4), Jul./Aug. 1998, p917-928, the melt elasticity of polymer melts is of great importance for many polymer processes like fiber spinning, film blowing, blow molding, high-speed coating, and sheet casting. A measure of melt elasticity can be made by the use of an "extension diagram," where the drawdown force needed for elongation of an extruded strand of melted polymer is measured as a function of a increasing drawdown speed. For this purpose, a tensile tester, the so-called "Rheotens," was developed (e.g., see Meissner, Rheol. Acta 10, 1971, p230-242). The Rheotens test is readily performed, shows excellent reproducibility, and models industrial polymer processes like fiber spinning or film casting. Therefore, the Rheotens test has found widespread application.

In a Rheotens test a strand of polymer melt extruded by a polymer melt viscometer is elongated under the action of rotating wheels which have gripped the meltstrand when the velocity of the wheels is larger than the output velocity of the strand. Normally the wheels are accelerated till the strand breaks or the maximum rotational speed of the wheels is obtained. A direct conversion of the tensile-force/drawdown-speed diagram into a relation between elongational viscosity and elongation rate is not possible. However, a considerable simplification in the analysis of constant force extension resulted from the discovery of "Rheotens mastercurves" for thermorheologically simple polymer melts (Wagner, et al., Polym. Eng. Sci. 36, 1996, p925-935). Rheotens mastercurves provide a basis for a direct and quantitative comparison of the elasticity of polymer melts under processing conditions.

Surprisingly, even for Rheotens experiments performed at different extrusion pressures (termed extrusion "stress" in the art), Rheotens mastercurves can be found, if force and draw ratio are scaled appropriately as reported by Wagner, et al. Such mastercurves, which represent mastercurves of mastercurves, are termed "Rheotens supermastercurves." Wagner and Bernnat showed that the concept of Rheotens mastercurves could be generalized to experiments with extrusion dies and spinlines of different length, and that information on the elongational viscosity of polymer melts could be extracted from Rheotens mastercurves by use of an analytic rheological model.

Instruments for performing the Rheotens test are commercially available from Goettfert Inc., Parkway Rock Hill, S.C. However, the commercially available instrument for performing the Rheotens test is relatively expensive because it employs a polymer viscometer to generate the meltstrand. Furthermore, such instruments are considered by the art to be more useful in a research laboratory than in a quality control laboratory of a polymer production facility due to the expense of the instrument and the degree of skill needed to operate the instrument. Thus, there is a need for the development of a less expensive and more readily operated instrument for the determination of melt elasticity of a thermoplastic polymer.

SUMMARY OF THE INVENTION

This disclosure provides a method and apparatus for the determination of a standardized melt elasticity of a thermoplastic polymer which are less expensive and more readily operated than the Rheotens test and instrument of the prior art. More specifically, the disclosed invention is a method for determining a standardized melt elasticity value for a thermoplastic polymer, comprising the steps of: (a) heating the thermoplastic polymer to melt the thermoplastic polymer; (b) subjecting the melted thermoplastic polymer to a selected constant stress so that the melted thermoplastic polymer flows through a channel to form a strand of melted thermoplastic polymer leaving the channel at a velocity $V_0$, the selected constant stress and melted polymer temperature being in a range so that $V_0$ is greater than 1.27 millimeters per second, the channel having a diameter of about 2.1 millimeters and a length of about 8 millimeters; and (c) stretching the strand of melted thermoplastic polymer by applying a force to the strand of melted thermoplastic polymer to produce a stretched strand of thermoplastic polymer traveling at a velocity of about $33V_0$, the standardized melt elasticity value of the thermoplastic polymer being equal to the force.

The disclosed invention is also an apparatus for determining a standardized melt elasticity value for a thermoplastic polymer, comprising: (a) a frame; (b) a body defining a cylindrical barrel shaped depression in the body from the top of the body, the body defining a channel at the bottom of the body in communication with the cylindrical barrel shaped depression, the body attached to the frame; (c) a heater in thermal communication with the body for heating the body; (d) a dead weighted cylindrical piston dimensioned to fit into the cylindrical barrel shaped depression; (e) a position sensor for sensing the dynamic vertical position of the dead weighted cylindrical piston in the cylindrical barrel shaped depression; (f) a tension roller; (g) a load cell, the tension roller connected to the load cell, the load cell attached to the frame; (h) a guide roller attached to the frame; (i) an electrical speed controlled motor attached to the frame; (j) a pull roller driven by the motor, so that when a thermoplastic polymer is placed in the cylindrical barrel shaped depression followed by the dead weighted piston, the polymer melts and flows through the channel by the force of the constant stress of the dead weighted piston on the melted polymer to form a strand of melted polymer leaving the channel at a velocity $V_0$ determined from the dimensions of the channel and the rate of piston movement, the weight of the dead weighted piston and the temperature of the melted polymer being in a range so that $V_0$ is greater than 1.27 millimeters per second, so that the strand of polymer can be passed under the tension roller, over the guide roller and onto the pull roller, the pull roller being driven at a rate so that the strand of melted thermoplastic polymer is stretched to form a solidified stretched strand of thermoplastic polymer having a velocity of about $33V_0$, so that the melt elasticity value of the thermoplastic polymer can be standardized as being equal to the stretching force measured by the load cell.

DETAILED DESCRIPTION

Figure 1:
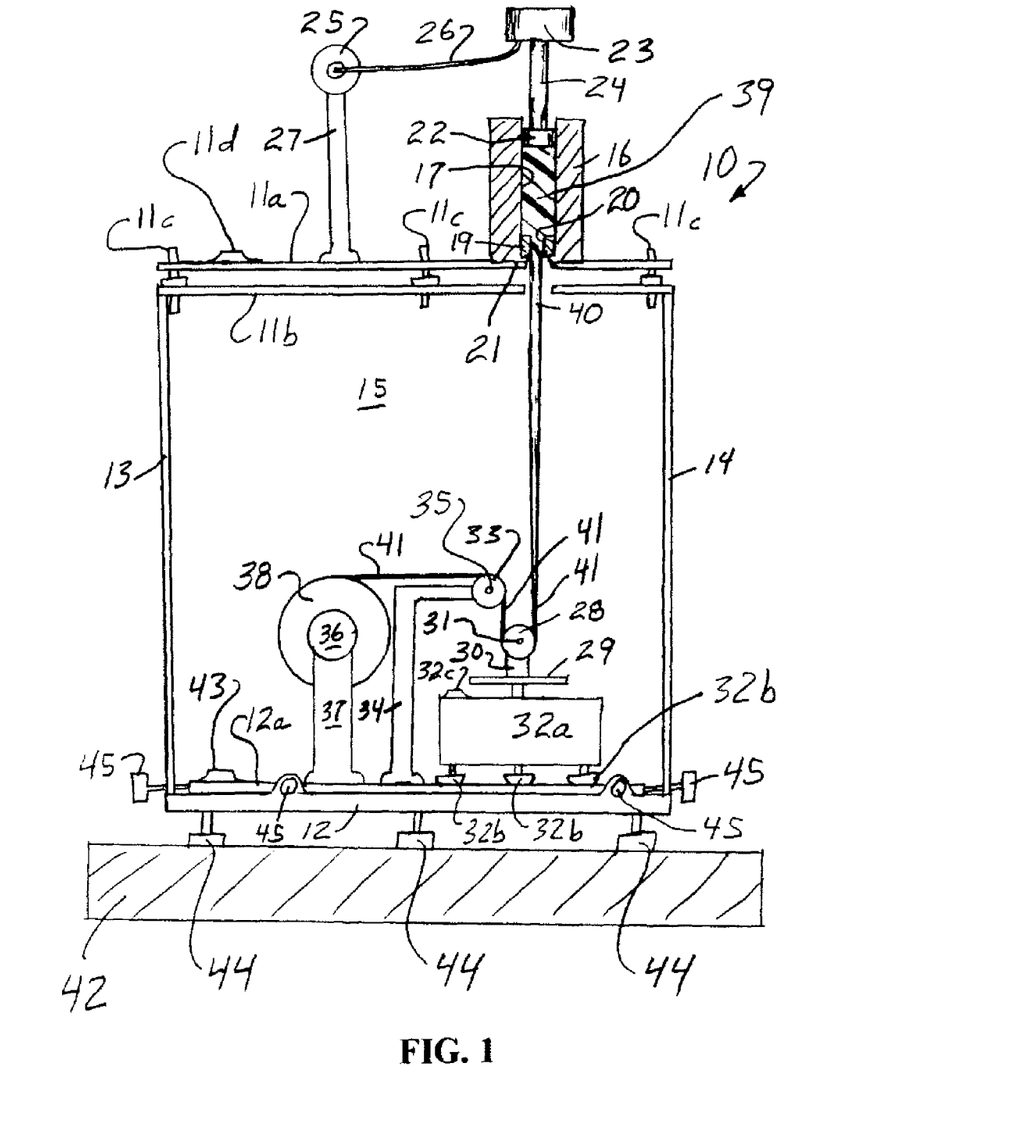
FIG. 1 is a front view, part in full and part in cross section of an apparatus of this disclosure.

Referring now to FIG. 1, therein is depicted an apparatus 10 for determining a standardized melt elasticity value for a thermoplastic polymer according to the instant disclosure. The apparatus 10 is based on a frame having an upper top section 11a, a lower top section 11b, a bottom 12, a sliding base plate 12a, a left side 13, a right side 14 and a back 15. The upper top section 11a is attached to lower top section 11b by leveling bolts 11c and leveled using top two dimensional bubble level 11d. An electrically heated body 16 defining a cylindrical barrel shaped depression 17 is attached to the upper top section 11a. The operating temperature of the body 16 preferably ranges from 125-390° C. as prescribed by ASTM test method D 1238-4 based on the specific melting point for each polymer type. Although each polymer type may use a different body temperature (for example, 190° C. for polyethylene), the Melt Flow Rate method specifies a constant preheat time of 7 minutes±30 seconds for all polymer types in order to minimize the impact of degradation and cross-linking on measurement results. However, it is understood by those skilled in the art that different preheat times may be required to perform non-standardized melt flow tests or for polymers that are more or less sensitive to thermal influence.

Figure 3:
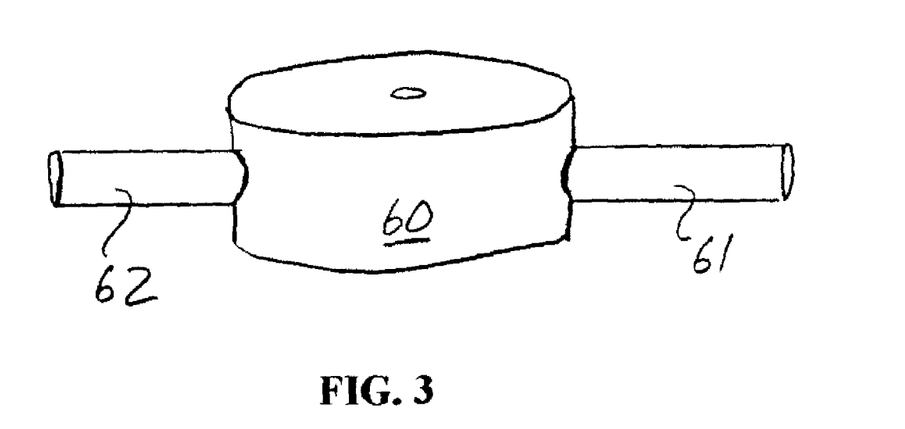
FIG. 3 is a perspective view in full of a weight of this disclosure having handles.
Figure 8:
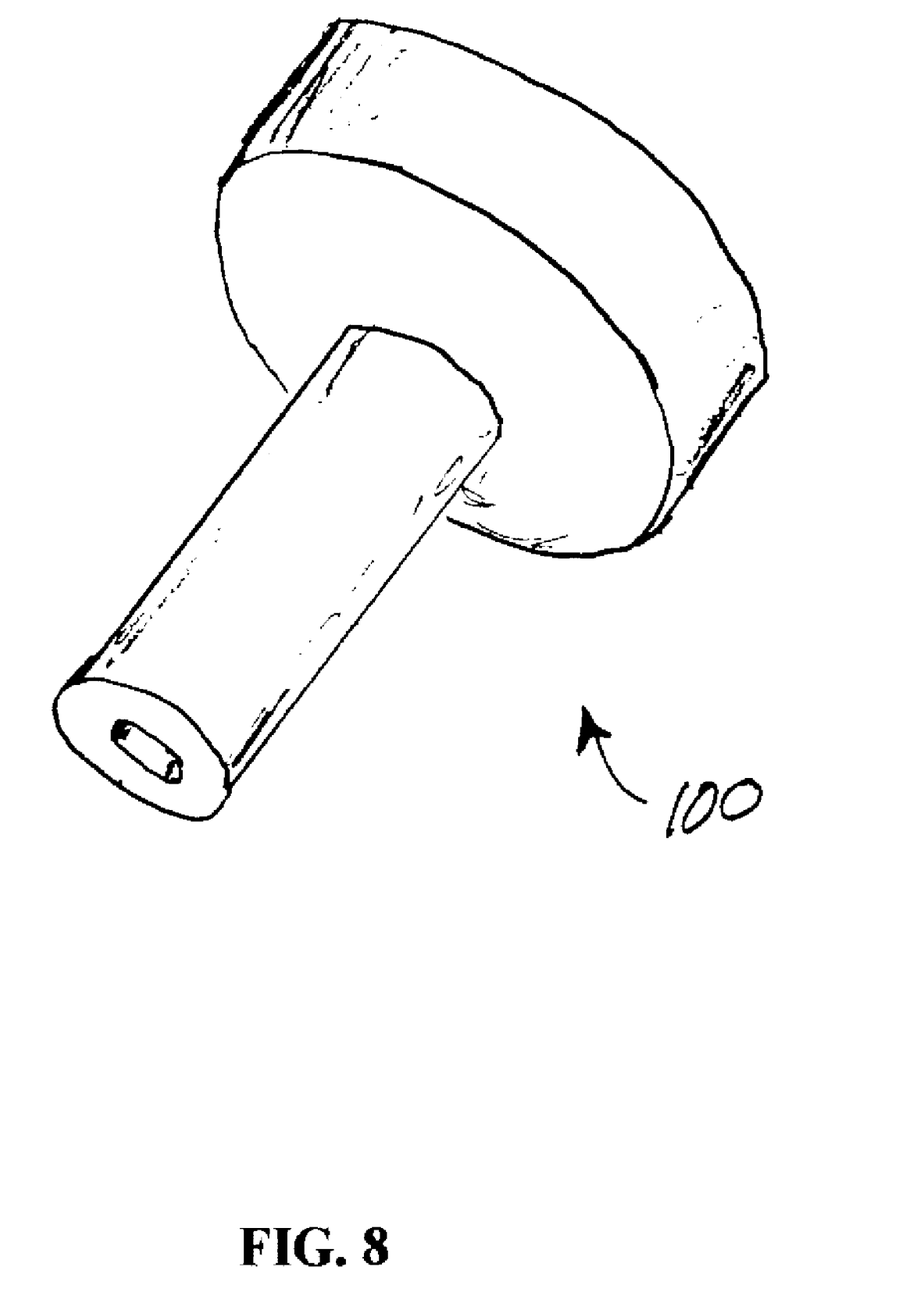
FIG. 8 is a perspective view in full of a tool used to set the horizontal position of the piston position sensor of the apparatus shown in FIG. 1.

The body 16 comprises a die 19 defining a channel 20 with a diameter of 2.095±0.0051 millimeters and a length of 8.000±0.025 millimeters at the bottom 21 of the body 16, the channel 20 in communication with the cylindrical barrel shaped depression 17. A piston 22, weighted by an unencumbered dead weight 23 and connecting rod 24, is dimensioned to fit into the cylindrical barrel shaped depression 17. The unencumbered dead weight 23 can alternatively be configured as shown in FIG. 3 to include handles 61 and 62 connected to weight 60. The handles 61 and 62 can be used to facilitate the movement of the piston 22 to pre-defined barrel start positions for both the standardized melt elasticity and melt flow rate methods. A position sensor 25 for sensing the dynamic vertical position of the piston 22 relative to the top of the die 19 by way of a feeler rod 26 is supported on the upper top section 11a by support 27. FIG. 8 shows a perspective view in full of a tool 100 made of stainless steel that is used to set the horizontal position of the position sensor 25 by setting the tool 100 on top of the piston 22 in place of the weight 23. Since the elements 16-27 are commercially available as the Tinius Olsen (Horsham, Pa.) Model MP600 Plastometer, which is designed to conform to the requirements of ASTM test method D1238-04, the Melt Flow Rate of a melted polymer 39 can be determined after the standardized melt elasticity is determined.

Referring to FIG. 1, a tension roller 28 is connected to platform 29 by way of mount 30. The platform 29 weighs about 175 grams and is attached to a load cell 32a (For example, the Mettler Toledo (Columbus, Ohio) Model X52035 electronic balance) having hemisphere ended leveling bolts 32b resting in corresponding depressions in sliding base plate 12a, so that the load cell 32a can be leveled using two dimensional level 32c. The tension roller 28 incorporates a low friction instrument grade ball bearing 31. The tension roller 28 is made of anodized aluminum, has a diameter of twenty five millimeters, a thickness of three millimeters and a circumferential one millimeter deep v-groove. A guide roller 33 is attached to base plate 12a by mount 34. The guide roller 33 is made of anodized aluminum, has a diameter of twenty five millimeters, a thickness of three millimeters and a circumferential one millimeter deep v-groove. The guide roller 33 incorporates a low friction instrument grade ball bearing 35. The use of the instrument grade ball bearings 31 and 35 and the careful alignment of the mounts 30 and 34 reduce to a minimum any frictional error in the final method result. An electrical motor 36 (For example, the Oriental Motor (Torrance, Calif.) Model RK564AA-T7.2) is attached to base plate 12a by mount 37. A pull roller 38 is driven by the motor 36. The pull roller 38 has the shape of a truncated cone having a circumference at its large end of about one hundred and twenty five millimeters, a width of about fifty millimeters and a slope of about 0.5 degrees so that the solidified stretched strand 41 winds up onto the pull roller 38 in a single layer.

Referring to FIG. 1, when a thermoplastic polymer is placed into the cylindrical barrel shaped depression 17 followed by the dead weighted piston 22, the polymer melts to form melted polymer 39 which flows through the channel 20 by the force of the constant stress of the dead weighted piston 22 on the melted polymer 39 to form a strand of melted polymer 40 exiting from channel 20 at a velocity $V_0$ determined from the dimensions of the channel 20 and the rate of piston 22 movement with the weight of the dead weighted piston 22 and the temperature of the melted polymer 39 being in a range so that $V_0$ is greater than 1.27 millimeters per second. The strand of melted polymer cools while being stretched to form a solidified stretched polymer 41 which is passed under the tension roller 28, over the guide roller 33 and onto the pull roller 38. The pull roller 38 is driven at a rate so that the strand of melted thermoplastic polymer 40 is stretched to form the strand of solidified stretched polymer 41 having a velocity in the range of $32.6$-$33.6V_0$, so that the melt elasticity value of the thermoplastic polymer can be standardized as being equal to the drawdown force measured in centi-Newtons (cN) by way of the absolute value of the gram-force measurement made by load cell 32 (the conversion factor is 0.980665 centi-Newtons per gram). Preferably, the velocity of the stretched strand of thermoplastic polymer is linearly ramped from about $25V_0$ to about $40V_0$ over a period of time of about one minute, the standardized melt elasticity of the thermoplastic polymer being equal to the drawdown force when the velocity of the solidified stretched strand of thermoplastic polymer is in the range of $32.6$-$33.6V_0$. Such ramping protocol facilitates analysis even when the melt flow rate of a polymer sample deviates somewhat from its expected value.

Figure 6:
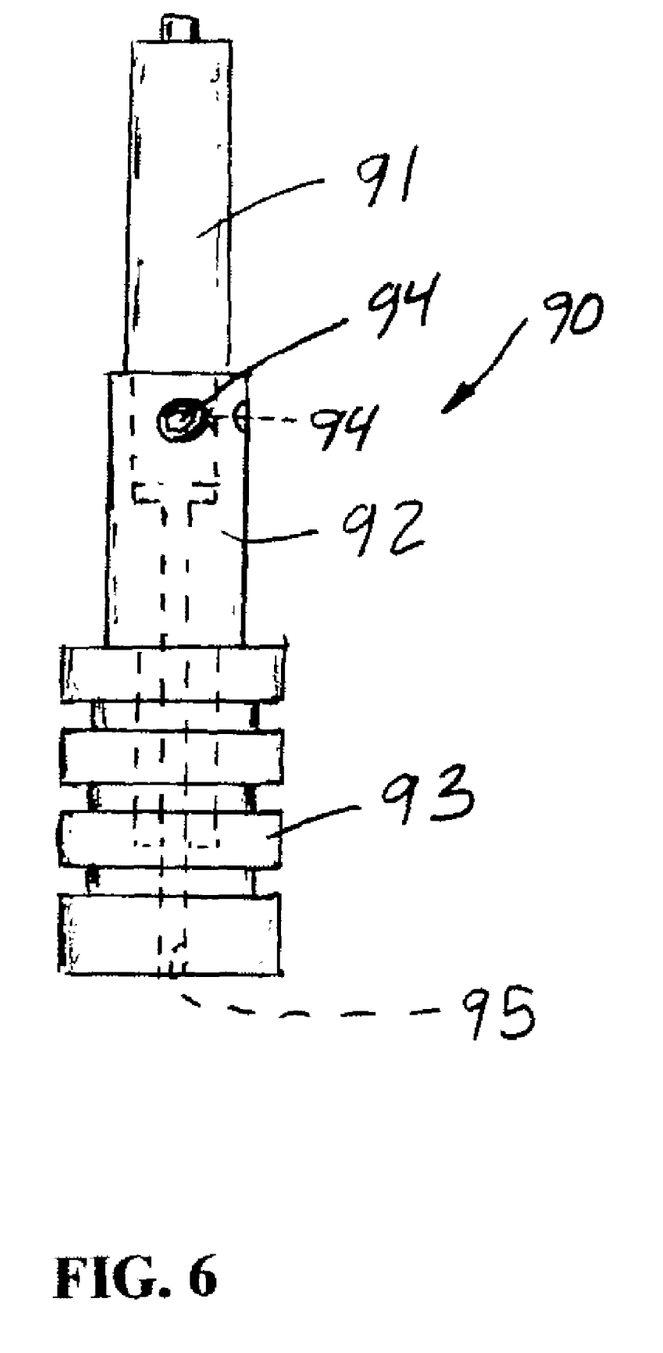
FIG. 6 is a side view, part in full and part hidden, of a laser alignment tool used to set-up the apparatus shown in FIG. 1.

Referring to FIG. 1, leveling screws 44 are adjusted to support the bottom 12 on support 42 in a level position as determined by an integrated two dimensional bubble level 43. Adjusting screws 45 are used to adjust slidable base plate 12a so that the v-groove of the tension roller 28 is directly below the channel 20 using a laser bore scope system carefully aligned with the longitudinal axis of the depression 17 when the body 16 is at its operational temperature so that a laser beam directed through the channel 20 just strikes the v-groove of the tension roller 28. FIG. 6 shows a suitable laser bore scope system 90 consisting of a stainless steel heat sink 93, a heat resistant polyamide-imide polymer adapter 92 made of TORLON brand engineering polymer (Parkway Products Inc., Florence Ky.) and a laser bore scope 91. The adapter 92 protects the laser bore scope 91 from overheating when the laser bore scope system 90 is inserted into the depression 17. The laser bore scope 91 is adjusted to center the laser beam from the laser bore scope 91 through bore 95 and the center of the channel 20 by adjustment of alignment screws 94 of the laser bore scope 91. The laser bore scope 91 is commercially available from Midway USA, Columbia, Mo. Not shown in FIG. 1 is a Plexiglas shield positioned across the front of the apparatus 10 so that vagrant air currents do not interfere with the analysis.

Figure 5:
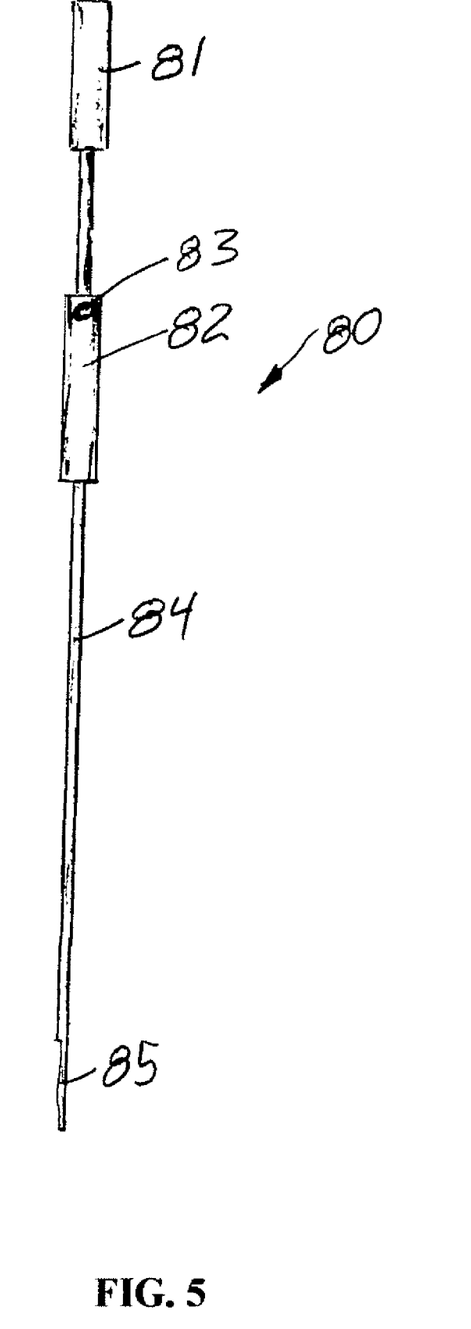
FIG. 5 is a side view of a melt strand length adjustment gauge used for initial installation and set-up of the apparatus shown in FIG. 1.
Figure 7:
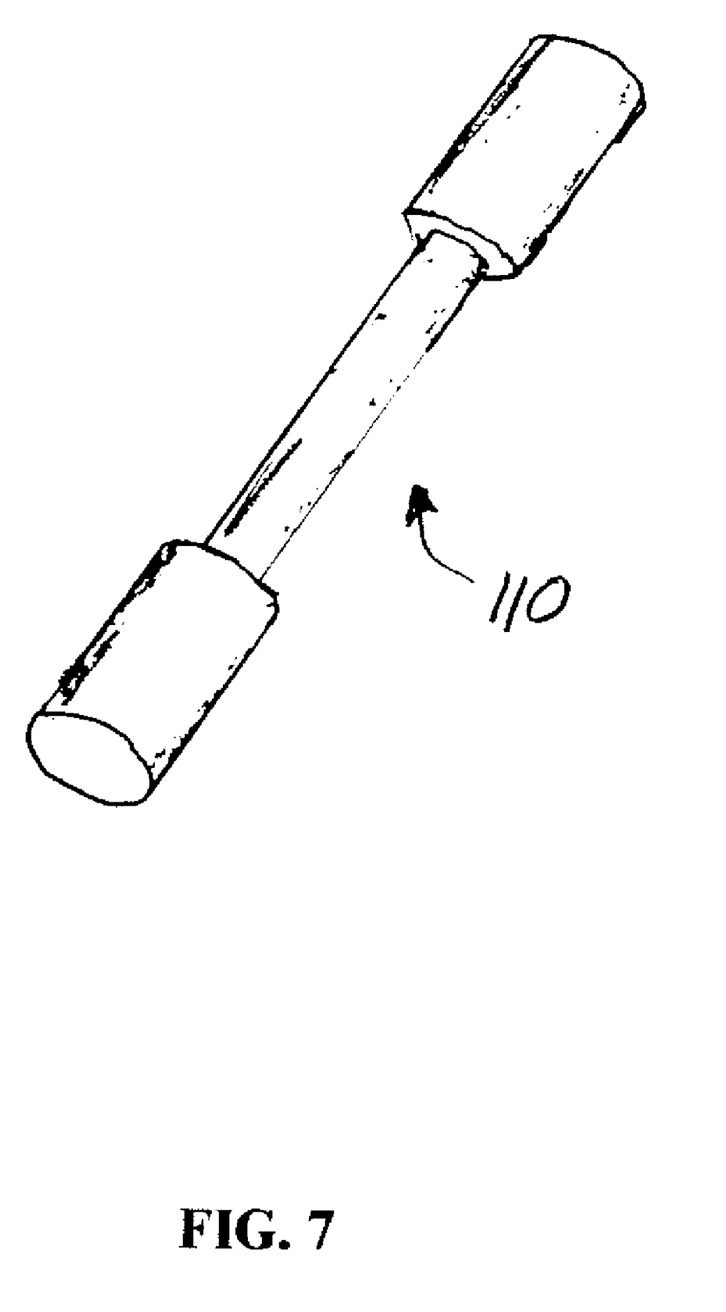
FIG. 7 is a perspective view in full of a tool used to confirm the temperature recovery response of the heated body of the apparatus shown in FIG. 1.

Referring to FIG. 5, the distance between the bottom of the body 21 and the platform 29 is preferably carefully adjusted to be four hundred and forty five millimeters resulting in the distance between the bottom of the body 21 and the horizontal center line of the bearing 31 preferably being four hundred and twenty four millimeters to further standardize the apparatus and promote solidification of the polymer prior to contact with the tension roller 28 by inserting the melt strand length adjustment gauge 80 into an empty depression 17 and adjusting leveling bolts 11c until the load cell 32a just indicates that platform 29 is being depressed. The melt strand length adjustment gauge 80 shown in FIG. 5 consists of a stainless steel rod 84 having a brass handle 81 at one end thereof and a twenty five millimeter long half round portion 85 at the other end. A stainless steel sleeve 82 is held in place on the rod 84 by a set screw 83. The half round portion 85 allows the tool 80 to slide down past the tension roller 28 without vertical deviation. FIG. 7 shows a solid brass temperature recovery standard 110 dimensioned to fit into the depression 17 for defining and validating control parameters governing the rate of temperature recovery by the electrically heated body 16 of FIG. 1.

Figure 2:
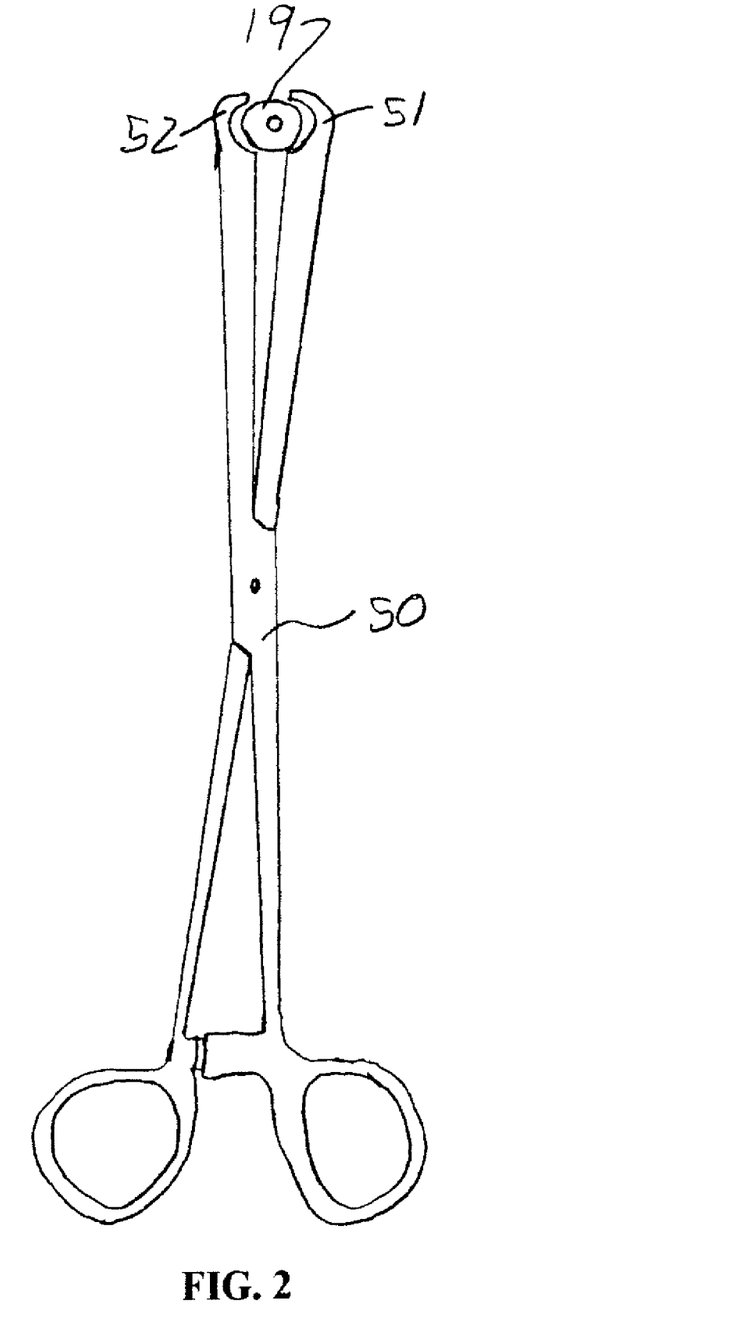
FIG. 2 is an upper view in full of a tool of this disclosure.

FIG. 2 shows an upper view in full of a tool 50 that can be used to safely secure the hot die 19 when it is removed from the electrically heated body 16 of FIG. 1 for cleaning following the measurement of standardized Melt Elasticity and Melt Flow Rate. The tool 50 possesses modified clamp tips 51 and 52 specifically designed to securely grasp the hot die 19 with the top and bottom surfaces exposed as well as the entrance and exit of channel 20. The tool 50 is fabricated by modifying a commercially available hemostat (Lakeside Scissor Sales, Sacramento, Calif.) and eliminates the need for thermal resistant gloves to directly handle the hot die 19 while removing residual sample material between analyses.

Figure 4:
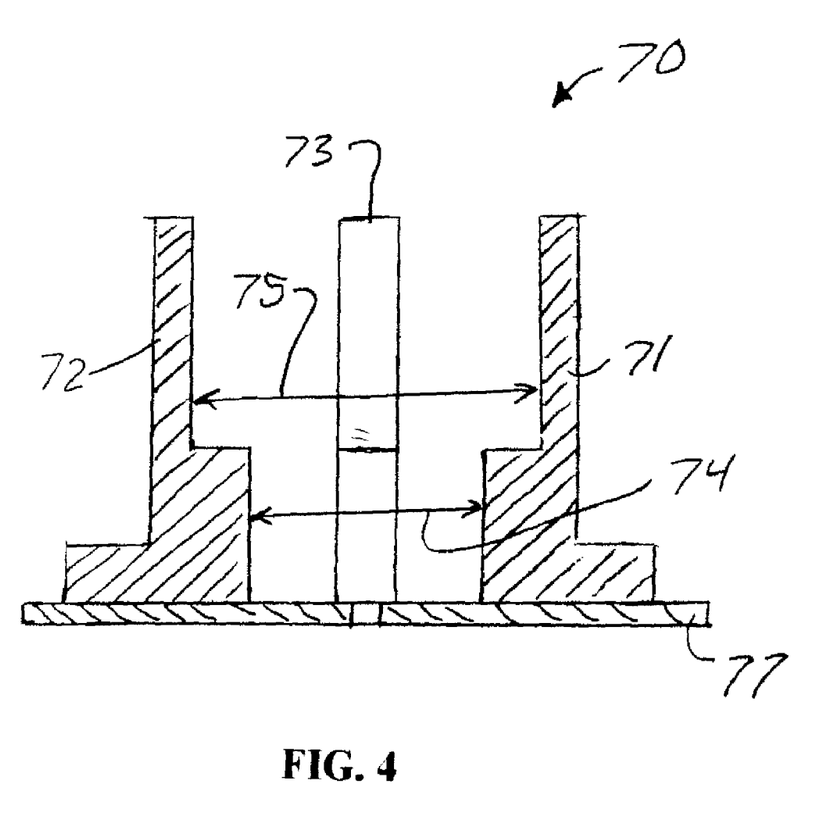
FIG. 4 is a side cross-sectional view of a weight guide of this disclosure.

FIG. 4 shows a cross-sectional side view of a modified dual weight management restraint system 70 for use with the above disclosed Tinius Olsen plastometer. The individual brackets 71, 72 and 73 replace the original guide rods situated on the automatic weight lifter platform 77. The modified dual weight management restraint system 70 includes a fourth identical bracket not shown in FIG. 3, which is symmetrically positioned directly in front of bracket 73. While space 74 is dimensioned to hold a smaller weight, Space 75 is dimensioned to hold a larger weight which can be combined with the smaller weight when the weight lifter platform 77 is sufficiently lowered.

Referring to FIG. 1, all electric components comprising apparatus 10 are preferably programmed to control the parameters disclosed above using a general purpose digital computer (Dell Model GX520) configured with four serial ports, 512 MB of RAM, a 3.4 GHZ processor and an 80 GB hard drive. In addition, apparatus 10 is significantly less expensive than an apparatus for performing the Rheotens test primarily because the polymer viscometer required in the Rheotens test instrument is much more expensive than the elements 16-27.

EXAMPLE

The origin of the six different samples (Samples 1-6) of commercial grade low density polyethylene having melt flow rates (MFR) tested using ASTM D 1238, condition 190° C./2.16 kg in the range of from about 0.7 to about 8.7 dg/min used to validate the performance of apparatus 10 are described in Table 1.

TABLE 1

| Sample # | ~MFR | Source | Country of Production |
|---|---|---|---|
| 1 | 0.7 dg/min | TDCC | Spain |
| 2 | 1.0 dg/min | TDCC | The Netherlands |
| 3 | 1.9 dg/min | TDCC | United States of America |
| 4 | 7.0 dg/min | TDCC | The Netherlands |
| 5 | 8.0 dg/min | TDCC | United States of America |
| 6 | 8.7 dg/min | TDCC | The Netherlands | where TDCC is The Dow Chemical Company

Samples 1-6 are analyzed for both standardized melt elasticity and melt flow rate using apparatus 10 shown in FIG. 1 under the specific conditions described in Table 2.

TABLE 2

| Sample # | Sample wt. | Body temp. | Piston wt. | Pull Roller Speed | Die Speed ($V_0$) |
|---|---|---|---|---|---|
| 1 | 5 grams | 190° C. | 5.00 Kg. | 64.72 mm/sec. | 1.95 mm/sec |
| 2 | 6 grams | 190° C. | 5.00 Kg. | 92.45 mm/sec. | 2.79 mm/sec |
| 3 | 5 grams | 190° C. | 2.16 Kg. | 42.02 mm/sec. | 1.27 mm/sec |
| 4 | 7 grams | 190° C. | 2.16 Kg. | 157.6 mm/sec. | 4.75 mm/sec |
| 5 | 7 grams | 190° C. | 2.16 Kg. | 168.1 mm/sec. | 5.06 mm/sec |
| 6 | 7 grams | 190° C. | 2.16 Kg. | 182.8 mm/sec. | 5.51 mm/sec |

The analysis precision for standardized melt elasticity (sME) in centi-Newtons [cN] of each sample is determined from ten replicates and reported in Table 3 below.

TABLE 3

| Sample # | Average sME | Relative STDEV |
|---|---|---|
| 1 | 9.05 cN | 0.72% |
| 2 | 7.35 cN | 0.56% |
| 3 | 3.36 cN | 0.68% |
| 4 | 2.76 cN | 0.87% |
| 5 | 2.44 cN | 1.07% |
| 6 | 2.19 cN | 1.32% |

What is claimed:

1. A method for determining a standardized melt elasticity value for a thermoplastic polymer, comprising the steps of: (a) heating the thermoplastic polymer to melt the thermoplastic polymer; (b) subjecting the melted thermoplastic polymer to a selected constant stress so that the melted thermoplastic polymer flows through a channel to form a strand of melted thermoplastic polymer leaving the channel at a velocity $V_0$, the selected constant stress being in a range so that $V_0$ is greater than 1.27 millimeters per second, the channel having a diameter of about 2.1 millimeters and a length of about 8 millimeters; and (c) stretching the strand of melted thermoplastic polymer by applying a force to the strand of melted thermoplastic polymer to produce a stretched strand of thermoplastic polymer traveling at a velocity of about $33V_0$, the standardized melt elasticity value of the thermoplastic polymer being equal to the force.

2. The method of claim 1, where the channel has a diameter of 2.095±0.0051 millimeters and a length of 8.000±0.025 millimeters and where the stretched strand of thermoplastic polymer is a solidified stretched strand of thermoplastic polymer traveling at a velocity in the range of $32.6$-$33.6V_0$.

3. The method of claim 1, where the stretched strand of thermoplastic polymer is a solidified strand of thermoplastic polymer having a velocity which is linearly increased from about $25V_0$ to about $40V_0$ over a period of time of about one minute, the standardized melt elasticity of the thermoplastic polymer being equal to the force when the velocity of the stretched strand of solidified thermoplastic polymer is about $33V_0$.

4. The method of claim 2, where the velocity of the solidified stretched strand of thermoplastic polymer is linearly increased from about $25V_0$ to about $40V_0$ over a period of time of about one minute, the standardized melt elasticity of the thermoplastic polymer being equal to the force when the velocity of the solidified stretched strand of thermoplastic polymer is in the range of $32.6$-$33.6V_0$.

5. The method of claim 1, where the temperature of step (a) is in the range of from 125-390° C.

6. The method of claim 3, where the temperature of step (a) is in the range of from 125-390° C.

7. The method of claim 4, where the temperature of step (a) is in the range of from 125-390° C.

8. The method of claim 1, where the duration and temperature of step (a) is about seven minutes at about 190° C.

9. The method of claim 3, where the duration and temperature of step (a) is about seven minutes at about 190° C.

10. The method of claim 4, where the duration and temperature of step (a) is about seven minutes at about 190° C.

11. Apparatus for determining a standardized melt elasticity value for a thermoplastic polymer, comprising: (a) a frame; (b) a body defining a cylindrical barrel shaped depression in the body from the top of the body, the body defining a channel at the bottom of the body in communication with the cylindrical barrel shaped depression, the body attached to the frame; (c) a heater in thermal communication with the body for heating the body; (d) a dead weighted cylindrical piston dimensioned to fit into the cylindrical barrel shaped depression; (e) a position sensor for sensing the dynamic vertical position of the dead weighted cylindrical piston in the cylindrical barrel shaped depression; (f) a tension roller; (g) a load cell, the tension roller connected to the load cell, the load cell attached to the frame; (h) an guide roller attached to the frame; (i) an electric motor attached to the frame; (j) a pull roller driven by the motor, so that when a thermoplastic polymer is placed in the cylindrical barrel shaped depression followed by the dead weighted piston, the polymer melts and flows through the channel by the force of the constant stress of the dead weighted piston on the melted polymer to form a strand of melted polymer leaving the channel at a velocity $V_0$ determined from the dimensions of the channel and the rate of piston movement with the weight of the dead weighted piston and the temperature of the melted polymer being in a range so that $V_0$ is greater than 1.27 millimeters per second, so that the strand of polymer can be passed under the tension roller, over the guide roller and onto the pull roller, the pull roller being driven at a rate so that the strand of melted thermoplastic polymer is stretched to form a strand of thermoplastic polymer having a velocity of about $33V_0$, so that the melt elasticity value of the thermoplastic polymer can be standardized as being equal to the force measured by the load cell.

12. The apparatus of claim 11, where the channel has a diameter of about 2.1 millimeters and a length of about 8 millimeters.

13. The apparatus of claim 11, where the channel has a diameter of 2.095±0.0051 millimeters and a length of 8.000±0.025 millimeters.

14. The apparatus of claim 13, where the pull roller has the shape of a truncated cone.

15. The apparatus of claim 14, where the truncated cone pull roller has a circumference at its large end of about 125 millimeters, a width of about 50 millimeters and a slope of about 0.5 degrees, and where the tension roller has a diameter of about 25 millimeters and a circumferential groove.

* * * * *